United States Patent [19]

Pike et al.

[11] Patent Number: 5,354,896

[45] Date of Patent: Oct. 11, 1994

[54] CATALYSTS FOR REACTION OF EPOXIDES AND ACIDS

[75] Inventors: William C. Pike, Midland, Mich.; Clinton J. Boriack, Freeport; James A. Rabon, Jr., West Columbia, both of Tex.

[73] Assignee: The Dow Chemical Company, Midland, Mich.

[21] Appl. No.: 12,104

[22] Filed: Feb. 1, 1993

[51] Int. Cl.$^5$ ............................................. C07C 67/26
[52] U.S. Cl. .................................................... 560/209
[58] Field of Search ........................................ 560/209

[56] References Cited

U.S. PATENT DOCUMENTS

| | | | |
|---|---|---|---|
| 3,215,731 | 11/1965 | Bearden et al. | 560/209 |
| 3,340,290 | 9/1967 | Blanchard | 560/209 |
| 3,372,172 | 3/1968 | Winkelmann et al. | 560/209 |
| 3,549,562 | 12/1970 | Mindick et al. | 560/209 |
| 3,804,884 | 4/1974 | Jeffrey et al. | 560/209 |
| 4,479,877 | 10/1984 | Guter | 560/209 |

Primary Examiner—Paul J. Killos

[57] ABSTRACT

Strong base anion exchange resins that contain quaternary ammonium groups derived from higher molecular weight amines, such as triethylamine or tripropylamine instead of trimethylamine, have a higher reactivity for catalyzing the reaction of an epoxide compound with an acid compound to form an ester.

16 Claims, No Drawings

CATALYSTS FOR REACTION OF EPOXIDES AND ACIDS

BACKGROUND OF THE INVENTION

The present invention relates to an improved catalyst for reacting carboxylic acid compounds with epoxide compounds to make esters.

It is known to make esters, such as hydroxyalkylacrylates, by reacting an epoxide or alkylene oxide compound with a carboxylic acid compound. It is also known that anion exchange resins, such as resins that contain quaternary ammonium sites, are useful catalysts for catalyzing such a reaction. See, e.g., Wheeler et al., U.S. Pat. No. 3,340,295 (Sep. 5, 1967); and Jeffrey et al., U.S. Pat. No. 3,804,884 (Apr. 16, 1974), which are incorporated herein by reference.

The efficiency of such processes could be improved by increasing the activity of the catalyst for the reaction. Therefore, it would be desirable to find a catalyst with improved reactivity.

SUMMARY OF THE INVENTION

The present invention is a process for making an ester compound, comprising the step of contacting:
(a) an epoxide compound that contains at least one oxirane ring with
(b) an acid compound that contains an acid moiety,
(c) in the presence of an anion exchange resin that contains quaternary ammonium moieties
under conditions such that an ester is formed, wherein the quaternary ammonium moieties in the anionic exchange resin comprise a nitrogen atom linked to a polymer backbone and to 3 pendant organic moieties whose average combined formula weight is at least about 59.

The quaternary ammonium anion exchange resin is derived from a reaction product of a tertiary amine that contains at least one organic substituent larger than a methyl group. It has surprisingly been discovered that anion exchange resins derived from higher molecular weight tertiary amines have a higher catalyst activity than resins derived from commonly-used trimethylamine. The higher activity results in an improved catalytic process.

DETAILED DESCRIPTION OF THE INVENTION

The present invention uses an epoxide compound that contains at least one oxirane ring. Examples of suitable epoxide compounds include alkylene oxide compounds and epihalohydrin compounds. An alkylene oxide compound preferably contains 2 to 6 carbon atoms and is more preferably ethylene oxide, propylene oxide or butylene oxide. The epihalohydrin compound is preferably epichlorohydrin. The epoxide compound is preferably represented by formula 1

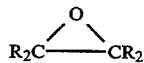   I wherein each R is independently a hydrogen atom, an alkyl group or a halogenated alkyl group.

The present invention also uses an acid compound that contains an acid moiety. Any acidic material that will react with the epoxide compound is suitable. Examples of suitable acid moieties include carboxylic acid groups and phenolic hydroxyl groups. The acid moiety is preferably a carboxylic acid group. The $pK_a$ of the acid moiety is preferably no more than about 10 and preferably at least about 1.8. The acid compound may contain two or more acid moieties, but it preferably contains on average about one acid moiety. The molecular weight of the acid compound is not critical to the present invention, but is preferably between about 60 and about 338. Examples of suitable acid compounds include acrylic and methacrylic acid.

The epoxide compound and the acid compound are reacted in the presence of a quaternary ammonium strong base anion exchange resin. Suitable ion exchange resins are already known for other purposes. The resin is preferably represented by formula II:

   II wherein:
Py represents a polymer backbone,
L represents a bond or a divalent organic moiety that links the ammonium group to the polymer backbone and that does not interfere with the making or use of the resin;
each Q independently represents an organic group,
X represents an anion counter-ion, and
"a" represents the average number of reactive sites linked to the polymer backbone (Py).

The polymer backbone (Py) should not interfere with the process, It should be substantially insoluble in the reagents that are used in the reaction, and it should be essentially stable under reaction conditions. It is preferably selected so that the anion exchange resin is a macroporous resin, rather than a gel resin. It preferably consists essentially of alkyl, acrylic, methacrylic and/or aromatic units. For example, the anion exchange resin may contain ammonium groups bonded either to acrylic repeating units or to benzylic carbon atoms on styrenic repeating units. Examples of suitable base polymers are described in Jeffrey, U.S. Pat. No. 3,804,884 (Apr. 16, 1974) and in Rabon et al., U.S. Pat. No. 4,970,333 (Nov. 13, 1990), which are incorporated herein by reference. The bond or linking group (L) has the same definition as the polymer backbone and may legitimately be thought of as a pendant extension of the polymer backbone.

The organic groups (Q) bonded to each nitrogen atom are selected so that they have an average combined formula weight of at least 59. The average combined formula weight of the Q groups is preferably at least about 73 and more preferably at least about 87. The organic (Q) groups should not interfere with the reaction; they are preferably essentially inert under reaction conditions. The organic (Q) groups are preferably alkyl groups, more preferably alkyl groups that contain 2 to 6 carbon atoms, and most preferably ethyl, propyl or butyl groups. The combined formula weight of the organic groups (Q) is preferably no more than about 255, more preferably no more than about 213 and most preferably no more than about 171. Two of the organic (Q) groups may optionally be linked so that a cyclic structure is formed.

The catalytic sites also contain an anion that serves as a counter ion for the quaternary ammonium site. The anion exchange resin is usually made with a halide anion (such as chloride) serving as the counter ion. That counter ion may be exchanged for another anion (such as a hydroxyl ion) before the reaction commences, if desired. However, under reaction conditions the initial counter ion is usually replaced by the anion corresponding to the acid compound that is used in the reaction. For instance, during the reaction of methacrylic acid or phenol, the counter ion will become a methacryloxy or a phenate anion, respectively.

The polymer should be bonded to enough reactive sites so that it can be an effective catalyst. The concentration of quaternary ammonium sites within the anion exchange resin is preferably at least about 1 meq of anion (as calculated by measuring chloride ion) per g of dry resin (meq/g) and more preferably at least about 2 meq/g. The concentration of quaternary ammonium sites within the anion exchange resin is preferably no more than about 4 meq/g.

Examples of suitable anion exchange resins can be made by known processes such as the processes described in Mindick et al., U.S. Pat. No. 3,549,562 (Dec. 22, 1970) and Guter, U.S. Pat. No. 4,479,877 (Oct. 30, 1984), which are incorporated herein by reference. In summary, a styrenic polymer, such as a styrene divinylbenzene polymer, that has pendant chloromethyl groups is reacted with an amine that is suitable to give the desired Q groups. For instance, trimethylamine would not be desirable for the present invention but triethylamine, tripropylamine or tributylamine would be desirable. We have surprisingly discovered that anion exchange resins which are derived from the higher-molecular-weight amines have a higher degree of activity than exchange resins derived from lower molecular weight amines.

The reaction takes place under known conditions, such as the conditions described in Wheeler et al., U.S. Pat. No. 3,340,295 (Sep. 5, 1967), Jeffrey, U.S. Pat. No. 3,804,884 (Apr. 16, 1974) and Rabon et al., U.S. Pat. No. 4,970,333 (Nov. 13, 1990), which are incorporated herein by reference. The reaction may be carried out in a solvent, but it is preferably carried out in an excess of the epoxide compound, which serves as a solvent as well. The reaction preferably uses at least about 1 mole of epoxide compound per mole of acid, more preferably at least about 2 moles of epoxide compound, and most preferably at least about 4 moles of epoxide compound. It is most efficient that the reaction not use more than about 8 moles of epoxide compound per mole of acid. The reaction temperature is preferably at least about 40° C. and more preferably at least about 75° C. The temperature is preferably no more than about 100° C. and more preferably no more than about 85° C. The pressure is irrelevant, as long as the reagents remain in a state suitable for reaction. The pressure is conveniently about atmospheric pressure. The residence time is preferably long enough to achieve at least a 90 percent conversion of the acid compound, more preferably long enough to achieve at least a 98 percent conversion, and most preferably long enough to achieve at least a 99 percent conversion.

The beneficial effects of this invention are further demonstrated by the following examples.

ILLUSTRATIVE EXAMPLES

The following examples are for illustrative purposes only and should not be taken as limiting the scope of either the specification or the claims. Unless otherwise stated all parts and percentages are by weight.

EXAMPLE A

Preparation of Ion Exchange Resin

Ion exchange resins were prepared by the following general procedure. A 100 g quantity of polystyrene copolymer with 4–7 percent divinylbenzene is swollen for 30 minutes in 500 g to 800 g of chloromethylmethylether. A 10 g to 60 g quantity of zinc chloride or ferric chloride is added. The mixture is maintained at 30° C.–55° C. for 1 to 4 hours. Thereafter, the mixture is cooled and washed with methanol. The resulting chloromethylated beads are stored in methanol.

Three different samples of the chloromethylated beads are heated for 3 hours at 40° C., and treated with excess 5 percent hydrochloric acid. The beads are swollen in dioxane for about 15 minutes. Then a twofold excess of trimethylamine, triethylamine or tri-N-propylamine is added to the beads as shown in Table 1. An amount of water equivalent to the amount of dioxane is added. The resulting slurry is heated at 60° C.–90° C. for 3 to 6 hours and then treated with 5 percent hydrochloric acid.

The characteristics of the resulting beads are shown in Table 1

TABLE I

| Sa. | Amine | DWC (meq/g) | WVC (meq/ml) | WRC (%) | Percent Substitution |
|---|---|---|---|---|---|
| a | trimethyl | 3.72 | 0.93 | 62.1 | 100 |
| 1 | triethyl | 3.05 | 0.79 | 60.8 | 95 |
| 2 | tripropyl | 2.17 | 0.63 | 59.4 | 76 | wherein DWC is the dry weight capacity of the resin as measured by titration, WVC is wet volume exchange capacity as measured by titration, and WRC is water retention capacity as measured by the weight difference between wet and dry beads.

EXAMPLE 1

A stainless steel reactor is charged with the amount of catalyst shown in Table II, after the catalyst has been washed in methanol and dried under vacuum. A 5 g quantity of acrylic acid, 42 g of hydroxypropylacrylate, and 140 g of propylene oxide are added to the reactor. The reactor is agitated at 80° C. for 40 minutes. The reactor is cooled and the reaction mixture is drained. Excess propylene oxide is stripped under vacuum and residual acid is determined by titration. The results of the reaction are shown in Table II. Sample "a" is not an example of the present invention.

TABLE II

| Sa. | Amine | catalyst (g) | Catalyst Reactive sites (meq) | Conversion of Acrylic Acid (AA) (%) | Conversion of AA per meq of catalyst | Relative Activity |
|---|---|---|---|---|---|---|
| a | trimethyl | 5.00 | 18.8 | 51.5 | 2.7 | 1.0 |
| 1 | triethyl | 5.95 | 18.1 | 77.4 | 4.3 | 1.6 |
| 2 | tripropyl | 8.25 | 17.9 | 90.5 | 5.1 | 1.9 |

The table shows that reactive sites within the scope of the present invention have a much higher activity for catalyzing the esterification reaction.

What is claimed is:

1. A process for making an ester compound, comprising the step of contacting:
   (a) an epoxide compound that contains at least one oxirane ring with
   (b) an acid compound that contains a carboxylic acid moiety or a phenolic hydroxyl moiety,
   (c) in the presence of an anion exchange resin that contains quaternary ammonium moieties
   under conditions such that an ester is formed, wherein the quaternary ammonium moieties in the anionic exchange resin comprise a nitrogen atom linked to a polymer backbone and to 3 pendant alkyl groups that each contain 2 to 6 carbon atoms.

2. The process of claim 1 wherein the epoxide compound contains a plurality of oxirane rings.

3. The process of claim 1 wherein the epoxide compound contains on average about 1 oxirane ring.

4. The process of claim 1 wherein the epoxide compound is an alkylene oxide or an epihalohydrin.

5. The process of claim 1 wherein the acid compound contains a plurality of acid moieties.

6. The process of claim 1 wherein the acid compound contains on average about 1 acid moiety.

7. The process of claim 1 wherein the acid moiety has a pKa of about 1.8 to 10.

8. The process of claim 1 wherein the acid moiety is a phenolic hydroxyl group.

9. The process of claim 1 wherein the acid moiety is a carboxylic acid group.

10. The process of claim 1 wherein the acid compound is acrylic or methacrylic acid.

11. The process of claim 1 wherein the anion exchange resin is a macroporous exchange resin that contains a moiety represented by the Formula:

$$Py\!-\!(L\!-\!NQ_3^+X^-)_a$$

wherein:
Py represents a polymer backbone,
L represents a bond or a divalent organic moiety that links the ammonium group to the polymer backbone and that does not interfere with the making or use of the resin;
each Q independently represents a organic group,
X represents an anion counter-ion, and
"a" represents the average number of reactive sites linked suitable to the polymer backbone (Py).

12. The process of claim 11 wherein each Q is independently an ethyl or propyl group.

13. The process of claim 11 wherein the polymer backbone contains acrylic, methacrylic or styrene repeating units.

14. The process of claim 11 wherein the anion counter-ion is a halogen.

15. The process of claim 11 wherein the anion exchange resin is derived from the reaction of (i) a polymer that contains pendant benzylic halogen atoms and (ii) a tertiary amine.

16. A process for making an ester compound, comprising the step of contacting:
   (a) an alkylene oxide or epihalohydrin with
   (b) an acrylic or methacrylic acid,
   (c) in the presence of an anion exchange resin that contains quaternary ammonium moieties
   under conditions such that an ester is formed, wherein the quaternary ammonium moieties in the anionic exchange resin comprise a nitrogen atom linked to a polymer backbone and to 3 ethyl, propyl, butyl, pentyl or hexyl groups.

* * * * *